(12) United States Patent
Inomata et al.

(10) Patent No.: US 8,420,066 B2
(45) Date of Patent: Apr. 16, 2013

(54) O/W EMULSION COSMETIC COMPOSITION

(75) Inventors: Yukio Inomata, Sumida-ku (JP); Toshio Uesaka, Sumida-ku (JP); Satoshi Sugawara, Sumida-ku (JP); Yasumitsu Sakuma, Wakayama (JP); Masahiro Umehara, Wakayama (JP)

(73) Assignee: Kao Corporation, Tokyo (JP)

( * ) Notice: Subject to any disclaimer, the term of this patent is extended or adjusted under 35 U.S.C. 154(b) by 885 days.

(21) Appl. No.: 12/089,611

(22) PCT Filed: Nov. 17, 2006

(86) PCT No.: PCT/JP2006/323508
§ 371 (c)(1),
(2), (4) Date: Apr. 9, 2008

(87) PCT Pub. No.: WO2007/058380
PCT Pub. Date: May 24, 2007

(65) Prior Publication Data
US 2009/0142383 A1  Jun. 4, 2009

(30) Foreign Application Priority Data
Nov. 18, 2005 (JP) .............................. 2005-334284

(51) Int. Cl.
*A61K 8/02* (2006.01)
*A61K 8/18* (2006.01)
*A61K 8/894* (2006.01)

(52) U.S. Cl.
USPC ..... 424/70.122; 424/401; 424/59; 424/70.12; 514/63; 514/844; 514/937

(58) Field of Classification Search .................. 424/401, 424/59, 70.12, 70.122; 514/844, 937, 938, 514/63
See application file for complete search history.

(56) References Cited

U.S. PATENT DOCUMENTS

| 4,906,458 | A | 3/1990 | Shigeta et al. |
| 6,197,282 | B1 * | 3/2001 | Oshima et al. ................. 424/59 |

FOREIGN PATENT DOCUMENTS

| EP | 0 953 336 | | 11/1999 |
| JP | 09 227331 | | 9/1997 |
| JP | 09227331 | A * | 9/1997 |
| JP | 11-012131 | | 1/1999 |
| JP | 2004 67581 | | 3/2004 |
| WO | 96 28137 | | 9/1996 |

OTHER PUBLICATIONS

Amazaki, K. et al. "Ultravilet-ray protective cosmetic", JP 09227331 A, Sep. 2, 1997, English translation (PTO 13-0046).*
U.S. Appl. No. 12/091,064, filed Apr. 22, 2008, Inomata, et al.

* cited by examiner

*Primary Examiner* — Gina C Justice
(74) *Attorney, Agent, or Firm* — Oblon, Spivak, McClelland, Maier & Neustadt, L.L.P.

(57) ABSTRACT

Provided is an O/W emulsion cosmetic composition, which contains the following components (A), (B) and (C):

(A) a polymer which is either a nonionic or cationic polymer composed of a hydrophobic monomer unit and a hydrophilic monomer unit and contains from 40 to 80 wt. % of a hydrophilic group;

(B) a dispersion containing the following components (a), (b), (c) and (d):
(a) powders having ultraviolet screening ability and having a surface subjected to hydrophobic treatment,
(b) a polymer composed of a hydrophobic monomer unit and a hydrophilic monomer unit,
(c) a silicone oil, and
(d) an alcohol having from 1 to 3 carbon atoms, at an (a):(b):(c):(d) weight ratio of (from 25 to 65):(from 0.1 to 5):(from 10 to 50):(from 10 to 50); and (C) water.

17 Claims, No Drawings

O/W EMULSION COSMETIC COMPOSITION

CROSS REFERENCES TO RELATED APPLICATIONS

This application is a 371 of International Patent Application No. PCT/JP2006/323508, filed on Nov. 17, 2006, and claims priority to Japanese Patent Application No. 2005-334284, filed on Nov. 18, 2005.

TECHNICAL FIELD

The present invention relates to an O/W emulsion cosmetic composition stably containing ultraviolet protection powders having a high specific gravity.

BACKGROUND ART

It is difficult to stably incorporate, in an O/W formulation having a non-greasy and refreshing feeling, powders highly effective for UV protection, for example, titanium oxide having a specific gravity of about 4.9 $g/cm^3$ or zinc oxide having a specific gravity of about 5.7 $g/cm^3$ because of its high specific gravity. Although thickening of its water phase has been investigated to solve this problem, an increase in the amount of such powders has resulted in failure.

For example, as described in Patent Document 1, an O/W cosmetic composition is prepared by dispersing hydrophobic ultraviolet protection powders in an oil component, and dispersing the powder dispersed phase in water by means of a thickener polymer having an emulsifying capacity. Such a cosmetic composition has however a high viscosity owing to the thickener polymer, and is not satisfactory in providing a refreshing feeling or cool feeling which the O/W cosmetic composition aims at. Moreover, such a cosmetic composition is not suited for use as a lotion or mist.
[Patent Document 1] JP-A-11-12131

DISCLOSURE OF THE INVENTION

In the present invention, there is thus provided an O/W emulsion cosmetic composition, which contains the following components (A), (B) and (C):

(A) a polymer which is either a nonionic or cationic polymer composed of a hydrophobic monomer unit and a hydrophilic monomer unit and contains from 40 to 80 wt % of the hydrophilic monomer unit;

(B) a dispersion containing the following components (a), (b), (c) and (d):

(a) powders having ultraviolet screening ability and having a surface subjected to hydrophobic treatment, (b) a polymer composed of a hydrophobic monomer unit and a hydrophilic monomer unit, (c) a silicone oil, (d) an alcohol having from 1 to 3 carbon atoms, at an (a):(b):(c):(d) wt ratio of (from 25 to 65):(from 0.1 to 5):(from 10 to 50):(from 10 to 50); and (C) water.

BEST MODE FOR CARRYING OUT THE INVENTION

The present invention relates to an O/W emulsion cosmetic composition which has a low viscosity but stably contains ultraviolet protection powders having a high specific gravity, and provides a refreshing and non-greasy feeling.

The present inventors have found that an O/W emulsion cosmetic composition which is stable in spite of having a low viscosity can be obtained by finely dispersing, in water, ultraviolet protection powders having a high specific gravity by means of a polymer having a specific balance between hydrophilicity and hydrophobicity.

The O/W emulsion cosmetic composition according to the present invention has a low viscosity but stably contains ultraviolet protection powders having a high specific gravity, provides a refreshing and non-greasy feeling and is highly effective for ultraviolet protection.

The polymer to be used as Component (A) in the present invention is either a nonionic or cationic polymer composed of a hydrophobic monomer unit and a hydrophilic monomer unit and it contains from 40 to 80 wt. %, preferably from 40 to 60 wt. % of the hydrophilic monomer unit. In this polymer, each of the hydrophobic monomer unit and hydrophilic monomer unit is preferably a macromer in which some same monomers have been polymerized. The hydrophobic macromer having a siloxane chain as a skeleton is more preferred. The hydrophilic macromer is preferably a polymer obtained by ring-opening polymerization of polyoxyethylene, polyoxypropylene or oxazoline. This polymer serves to emulsify, in water, an oil component having powders dispersed therein.

Specific examples of such a polymer include polyoxyethylene•methylpolysiloxane copolymer, poly(oxyethylene•oxypropylene) methylpolysiloxane copolymer, (polyoxyethylene alkylpolysiloxane) •(polyoxypropylene alkylpolysiloxan)•dimethylpolysiloxane copolymer, methylpolysiloxane•(alkyl methylpolysiloxane)•{poly(oxyethylene•oxypropylene) methylpolysiloxane} copolymer, amino-modified silicone and oxazoline-modified silicone.

Of these, oxazoline-modified silicone (poly-N-acylethyleneimine-modified silicone) as described in JP-A-7-133352 is preferred in order to stably and finely disperse the dispersion (B) in water.

The polymer (A) has a molecular weight preferably ranging from 10000 to 250000, more preferably from 10000 to 200000.

It is preferred to incorporate the polymer (A) in an amount of from 0.1 to 10 wt. %, more preferably from 0.2 to 5 wt. % in the entire composition, because within the above-described range, Component (B) can be dispersed stably, a high ultraviolet screening ability can be attained and the resulting composition can provide a pleasant feeling.

The dispersion (B) to be used in the present invention contains, at a predetermine ratio, (a) powders having ultraviolet screening capacity and having a surface subjected to hydrophobic treatment, (b) a polymer composed of a hydrophobic monomer unit and a hydrophilic monomer unit, (c) a silicone oil, and (d) an alcohol having from 1 to 3 carbon atoms.

The powders (a) having ultraviolet screening ability and having a surface subjected to hydrophobic treatment (which powders will hereinafter be called "hydrophobic UV protection powders") are obtained by subjecting powders having an ultraviolet screening ability to hydrophobic surface treatment. As the powders having UV screening ability, metal oxides effective for absorbing or scattering a wide range of ultraviolet rays from UVB to UVAII are preferred. Zinc oxide, titanium oxide and cerium oxide are more preferred because of their high ultraviolet absorbing or scattering effects. These metal oxides are preferably fine metal oxide particles. Their average particle size is preferably from 0.001 to 0.5 µm, more preferably from 0.01 to 0.1 µm.

Examples of the commercially available fine metal oxide particles include fine zinc oxide particles such as "FINEX-25", "FINEX-50", and "FINEX-75" (each, product of Sakai Chemical Industry), "MZ500 Series" and "MZ700 Series" (each, product of Tayca Corporation), and "ZnO-350" (product of Sumitomo Osaka Cement); fine titanium oxide particles such as "TTO-55 Series" and "TTO-51 Series" (each, product of Ishihara Sangyo Kaisha), and "JR series" and "JA series" (each, product of Tayca Corporation); and fine cerium oxide particles such as high-purity cerium oxide sold by Nikki and Seimi Chemical. Of these, zinc oxide and titanium oxide are preferred.

In the invention, the powders having ultraviolet screening ability are preferably under a dispersible state in the dispersion. To facilitate dispersion, the surface of the powders may be covered with another substance or the powders may be mixed with a dispersing assistant sol, for example, $Al_2O_3$ sol or a stabilizer of a sol. When ultrafine titanium oxide particles are employed, for example, dispersion stability can be heightened by covering the surface of the ultrafine particles with at least one oxide or hydrous oxide of an element selected from Al, Si, Zr, Mg, Zn, Ce, Ti and Fe.

The surface of the powders is subjected to hydrophobic treatment which is ordinarily given to powders for cosmetic compositions in order to improve resistance to sweat or water. No limitation is imposed on the surface treatment method insofar as it improves water repellency of the metal oxide. Examples of the method include treatment with silicone such as methyl hydrogen polysiloxane, dimethylpolysiloxane or silicone resin and treatment with a fluorine compound such as a perfluoro-containing compound.

As the polymer (b) composed of a hydrophobic monomer unit and a hydrophilic monomer unit, polymers as described above in Component (A) can be used. No particular limitation is imposed on the amount of the hydrophilic monomer unit, but it is preferably from 50 to 80 wt. %, more preferably from 10 to 60 wt. %. Similar to Component (A), the hydrophobic monomer unit and hydrophilic monomer unit each preferably constitutes a macromer. The polymer (b) may be the same as or different from the polymer (A), but it is preferably the same as the polymer (A).

No limitation is imposed on the silicone oil (c) insofar as it is used for ordinary cosmetic compositions, is liquid at 20° C., and is capable of dispersing the hydrophobic ultraviolet protection powders (a) therein.

Examples include dimethylpolysiloxane and methylcyclopolysiloxane. The silicone oil having a viscosity at 20° C. of from 1 to 1000 $mm^2$/s is preferred from the viewpoint of the feel to the touch.

Examples of the alcohol (d) having from 1 to 3 carbon atoms include methanol, ethanol and propanol. Of these, ethanol is preferred, but a mixture of them is usable.

The dispersion (B) contains (a), (b), (c) and (d) at an (a):(b):(c):(d) weight ratio of (from 25 to 65):(from 0.1 to 5):(from 10 to 50):(from 10 to 50), preferably (from 25 to 65):(from 0.5 to 4):(from 20 to 50):(from 10 to 50). Within the above-described range, a more stable dispersion can be obtained.

It is preferred to use the alcohol (d) having from 1 to 3 carbon atoms in an amount of from 0.5 to 5 times the weight of the silicone oil (c) in order to improve the dispersibility of the powders.

Components other than (a), (b), (c) and (d), for example, powders, oil component and ultraviolet absorbers other than the above-described ones may be added to the dispersion (B).

The dispersion containing the components (a), (b), (c) and (d) can be manufactured by mixing predetermined amounts of the components (a), (b), (c) and (d) and then stirring and mixing them vigorously by using an apparatus suited for it such as a mill, disper or (high-pressure) homogenizer.

The dispersion (B) is contained preferably in an amount of from 1 to 50 wt. %, more preferably from 5 to 30 wt. % in the entire composition. Within the above-described range, the resulting composition can exhibit ultraviolet protection effects efficiently.

The average particle size of the dispersion (B) in water is preferably as small as possible because if so, dispersion resulting from Brownian motion becomes stable. The average particle size is preferably 10 μm or less, more preferably 5 μm or less, even more preferably 1 μm or less. The average particle size is measured by a laser scattering particle size distribution analyzer.

In the present invention, in order to decrease the size of dispersion droplets of the dispersion in water and improve the stability of the dispersion, Component (A), polymer (b) and hydrophobic ultraviolet protection powders (a) are added preferably at a ratio satisfying the following equation: $((A)+(b))/(a) \geq 0.05$, more preferably $((A)+(b))/(a) \geq 0.1$.

The amount of water as Component (C) may be the balance, but it is preferably from 50 to 99 wt. %, more preferably from 70 to 95 wt. % in the entire composition. Within the above-described range, the resulting cosmetic composition can provide a refreshing and cool feeling.

The cosmetic composition of the present invention may contain an organic ultraviolet absorber further to improve the ultraviolet protection effects. No limitation is imposed on the organic ultraviolet absorber, but an oil soluble one is preferred.

The oil soluble ultraviolet absorbers include benzoic acid, anthranilic acid, salicylic acid, cinnamic acid and benzophenone ones. Examples of the benzoic acid ultraviolet absorber include para-aminobenzoic acid (which will hereinafter be abbreviated as PABA), glyceryl PABA, ethyl dihydroxypropyl PABA, N-ethoxylate PABA ethyl ester, N-dimethyl PABA ethyl ester, N-dimethyl PABA butyl ester, N-dimethyl PABA amino ester and octyldimethyl PABA. Those of the anthranilic acid one include homomethyl-N-acetyl anthranilate. Those of the salicylic acid one include amyl salicylate, menthyl salicylate, homomethyl salicylate, octyl salicylate, phenyl salicylate, benzyl salicylate and p-isopropanolphenyl salicylate. Those of the cinnamic acid one include octyl cinnamate, ethyl-4-isopropyl cinnamate, ethyl-2,4-diisopropyl cinnamate, methyl-2,4-diisopropyl cinnamate, propyl p-methoxycinnamate, isopropyl p-methoxycinnamate, isoamyl p-methoxycinnamate, 2-ethylhexyl p-methoxycinnamate, 2-ethoxyethyl p-methoxycinnamate, cyclohexyl p-methoxycinnamate, ethyl α-cyano-β-phenyl-cinnamate, 2-ethylhexyl α-cyano-β-phenylcinnamate and glyceryl mono-2-ethylhexanoyl di-para-methoxycinnamate. Those of the benzophenone one include 2,4-dihydroxybenzophenone, 2,2'-dihydroxy-4-methoxy-benzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone and 4-hydroxy-3-carboxybenzophenone. Additional examples include 3-(4'-methylbenzylidene)-dl-camphor, 3-benzylidene-dl-camphor, ethyl urocanate, 2-phenyl-5-methylbenzoxazole, 2,2'-hydroxy-5-methylphenylbenzotriazole, 2-(2'-hydroxy-5-t-octylphenyl)benzotriazole, dibenzaladine, dianisoylmethane, 4-methoxy-4'-t-butyl-dibenzoylmethane, 5-(3,3-dimethyl-2-norbornylidene)-3-pentan-2-one, benzene bis-1,3-diketone derivatives as described in JP-A-2-212579 and benzoylpinacolone derivatives as described in JP-A-3-220153.

The content of the organic ultraviolet absorber in the cosmetic composition is not limited, but is preferably from 0.1 to 25 wt. %, more preferably from 0.5 to 10 wt. % in the entire composition in order to heighten the ultraviolet protection effects and provide good feeling upon use.

The ultraviolet absorber may be added to the dispersion (B) or may be dispersed in water (C).

The O/W emulsion cosmetic composition of the present invention may stably contain hydrophobic powders having a high specific gravity in spite that it has a low viscosity. A thickener may however be added to such an extent not impairing the feeling upon use. As the thickener, (D) a nonionic polymer composed of a hydrophilic monomer unit can be used. As the nonionic polymer (D) composed of a hydrophilic monomer unit, those known as a cosmetic raw material are usable. Examples include guar gum, quince seed, carrageenan, xanthan gum, locust bean gum, gum arabic, tragacanth, pectin, mannan, starch, pullulan, dextran, curdlan, collagen, keratin, casein, albumin, gelatin, chitin, methyl cellulose, hydroxyethyl cellulose, hydroxypropyl cellulose, hydroxypropylmethyl cellulose, soluble starch, polyvinyl alcohol, polyvinylpyrrolidone, polyethylene glycol, polyvinylpyrrolidone, polyacrylic acid amide, and mucopolysaccharide and derivatives thereof.

One or more of these nonionic polymers (D) composed of a hydrophilic monomer unit can be used. From the viewpoints of giving a good feeling to the touch and improving the stability of the composition, Component (D) is added preferably in an amount of from 0.01 to 10 wt. %, more preferably from 0.05 to 5 wt. % in the entire composition.

The cosmetic composition of the present invention may further contain a surfactant. Nonionic surfactants are preferred. Examples of them include polyoxyethylene hydrogenated castor oil, polyoxyethylene alkyl ethers, polyoxyethylene alkyl phenyl ethers, polyoxyethylene glycol fatty acid esters, polyoxyethylene fatty acid esters, polyoxyethylene sorbitan fatty acid esters, polyoxyethylene fatty acid monoalkanolamides and polyoxyethylene fatty acid dialkanolamides.

The nonionic surfactant is incorporated preferably in an amount of from 0.1 to 5 wt. %, more preferably from 0.2 to 3 wt. % in the entire composition in order to dissolve or disperse another component therein stably.

The cosmetic composition according to the present invention can further contain an oil component. As the oil component, silicone oils, hydrocarbon oils, ester oils, ether oils and fluorinated oils are usable.

Examples of the silicone oil include linear polyorganosiloxanes and cyclic polysiloxanes. The linear polyorganosiloxanes include linear alkylpolysiloxanes having an alkyl group with 1 to 5 carbon atoms, and linear alkylarylpolysiloxanes having an alkyl group with 1 to 5 carbon atoms and an aryl group with 6 to 10 carbon atoms. Specific examples include linear dimethylpolysiloxane and linear methylphenylpolysiloxane. Of these linear organopolysiloxanes, those having a viscosity at 20° C. of from 1 to 1000 mPa·s are preferred, with those having a viscosity at 20° C. of from 5 to 10 mPa·s being more preferred. The cyclic polysiloxanes include 4- to 6-membered cyclic siloxanes having, as a substituent, an alkyl group with 1 to 5 carbon atoms. Specific examples include octamethylcyclotetrasiloxane and decamethylcyclopentasiloxane.

Examples of the hydrocarbon oil include liquid paraffin, squalane, light liquid isoparaffin, heavy liquid isoparaffin and polybutene.

Examples of the ester oil include plant oils such as safflower oil, soybean oil, grapeseed oil, perilla oil, wheat germ oil, avocado oil, olive oil, castor oil, Macadamia nut oil, and meadowfoam oil; animal oils such as mink oil, turtle oil and liquid lanoline; fatty acid esters of a lower alcohol such as isopropyl myristate, isopropyl isostearate and isopropyl lanolate; fatty acid esters of a higher alcohol such as 2-ethylhexyl isononanoate, isotridecyl isononanoate, octyldodecyl myristate, octyldodecyl oleate, cetyl 2-ethylhexanoate, isocetyl 2-ethylhexanoate, and isostearyl isostearate; oxyacid esters of a higher alcohol such as diisostearyl malate and cetyl lactate; and fatty acid esters of a polyol such as glyceryl tricaprylate, glyceryl tri-2-ethylhexanoate, glyceryl triisostearate, glyceryl(tricaprylate•caprate), propylene glycol dicaprylate, propylene glycol di(caprylate•caprate), propylene glycol diisostearate, neopentyl glycol dicaprate, and neopentyl glycol 2-ethylhexanoate.

Examples of the ether oil include cetyl dimethyl butyl ether, while those of the fluorinated oil include perfluoropolyether and perfluorocarbon.

Of these, silicone oils are preferred.

One or more of these oil components can be used and its (their) content in the entire composition is preferably from 0.01 to 30 wt. %, more preferably from 1 to 10 wt. %.

The cosmetic composition of the present invention may further contain components ordinarily employed for cosmetic compositions such as liquid oils, semisolid oils, alcohols, humectants, water soluble polymers, oil soluble polymers, polymer latexes, drugs, plant extracts, ceramides, blood circulation accelerators, cooling agents, antiperspirants, bactericides, skin activators, pH regulators, thickeners, antioxidants, antiseptics, and perfumes.

The cosmetic composition of the present invention stably contains ultraviolet protection powders having a high specific gravity in spite that it has a considerably low viscosity. Specifically, the viscosity of the composition can be adjusted to from 1 to 100 mPa·s, preferably from 1 to 50 mPa·s, more preferably from 1 to 20 mPa·s at 25° C. The viscosity can be measured using "B8L viscometer, Rotor No. 1, 30 rpm" manufactured by Toki Sangyo.

The O/W emulsion cosmetic composition of the present invention can be prepared in a conventional manner. It is suited as a low viscosity cosmetic composition such as a lotion or emulsion.

EXAMPLES

Preparation Example 1

Preparation of Oxazoline-Modified Silicone

In 550 g of dehydrated ethyl acetate were dissolved 7.57 g (0.049 mol) of diethyl sulfate and 263.3 g (2.66 mol) of 2-ethyl-2-oxazoline. Under a nitrogen atmosphere, the resulting solution was heated under reflux for 8 hours, whereby terminal-reactive poly(N-propionylethyleneimine) was synthesized. To the resulting product was added, in one portion, a 50% ethyl acetate solution of 250 g (0.065 mol in terms of an amino group) of a side-chain primary aminopropyl-modified polydimethylsiloxane (molecular weight: 60000 and amine equivalent: 3870), followed by heating under reflux for 12 hours. The reaction mixture was concentrated under reduced pressure, whereby an N-propionylethyleneimine-dimethylsiloxane copolymer was obtained as a pale yellow rubbery solid (505 g, yield: 97%). The copolymer had a weight average molecular weight of 88400 (hydrophilic macromer content: 49 wt. %).

Preparation Example 2

Preparation of Oxazoline-Modified Silicone

In 140 g of dehydrated ethyl acetate were dissolved 3.76 g (0.024 mol) of diethyl sulfate and 65.3 g (0.66 mol) of 2-ethyl-2-oxazoline. Under a nitrogen atmosphere, the resulting solution was heated under reflux for 8 hours to synthesize a terminal reactive poly(N-propionylethyleneimine). To the resulting product was added, in one portion, a 50% ethyl acetate solution of 500 g (0.024 mol in terms of an amino group) of a side-chain primary aminopropyl-modified polydimethylsiloxane (molecular weight: 100000 and amine equivalent: 20500), followed by heating under reflux for 12 hours. The reaction mixture was concentrated under reduced pressure, whereby an N-propionylethyleneimine-dimethylsiloxane copolymer was obtained as a pale yellow rubbery solid (537 g, yield: 95%). The copolymer had a weight average molecular weight of 149000 (hydrophilic macromer content: 12 wt. %).

Preparation Example 3

Preparation of Alkyl-Substituted Polysaccharide Derivative (1) A slurry solution was prepared by adding 50 g of hydroxyethyl cellulose ("HEC-QP4400", product of Union Carbide) having a weight average molecular weight of about 800000 and a hydroxyl substitution degree of 1.8, 400 g of 88% isopropyl alcohol and 3.5 g of a 48% aqueous solution of sodium hydroxide to a 1000-mL separable reaction container made of glass and equipped with a stirrer, thermometer and condenser tube. The resulting slurry solution was stirred at room temperature for 30 minutes under a nitrogen gas atmosphere. Hydrophobic treatment was then performed by adding 5.4 g of stearyl glycidyl ether to the reaction mixture and reacting the mixture at 80° C. for 8 hours. After completion of the hydrophobic treatment, the reaction mixture was neutralized with acetic acid, followed by filtration. The reaction product thus obtained was washed twice with 500 g of 80% acetone and then twice with 500 g of acetone, and dried for one day at 70° C. under reduced pressure, whereby 49.4 g of a hydrophobic hydroxyethyl cellulose derivative was obtained.

(2) In a 500-mL separable reaction container made of glass and equipped with a stirrer, a thermometer and a condenser tube were charged 10.0 g of the hydrophobic hydroxyethyl cellulose derivative obtained in (1), 80.0 g of isopropyl alcohol and 0.33 g of a 48% aqueous solution of sodium hydroxide to prepare a slurry solution. The resulting solution was stirred at room temperature for 30 minutes under a nitrogen gas stream. Sulfonation was performed at 50° C. for 9 hours by adding 6.4 g of sodium 3-chloro-2-hydroxypropanesulfonate, 2.7 g of a 48% aqueous solution of sodium hydroxide and 20.0 g of water to the reaction mixture. After completion of the reaction, the reaction mixture was neutralized with acetic acid, followed by filtration. The product thus obtained was washed three times with 500 g of 80% acetone (water: 20%), washed two times with 500 g of acetone, and dried for one day at 70° C. under reduced pressure, whereby 7.2 g of a water soluble polysaccharide derivative (1) substituted with a stearyl glyceryl ether group and a sulfo-2-hydroxypropyl group was obtained.

In the resulting water soluble alkyl-substituted polysaccharide derivative (1), the degree of substitution with the stearyl glyceryl ether group was 0.030, and that with the sulfo-2-hydroxypropyl group was 0.15. A ratio of the number of the substituents (a) in the hydrophobic portion and that of the substituents (b) in the hydrophilic portion was 30:150.

Preparation Example 4

Preparation of Component (B)

A mixture containing 34.1 wt. % of "S101-6 ZnO-350" (product of Daito Kasei) obtained by covering fine zinc oxide particles ("ZnO-350", product of Sumitomo Osaka Cement) with 6 wt. % (corresponding to 1.3 mg/m$^2$) of methyl hydrogen polysiloxane and 6.1 wt. % of "SI01-8 TT0-51A" (product of Daito Kasei) obtained by covering fine titanium oxide particles ("TT0-51A", product of Ishihara Sangyo Kaisha) with 8 wt. % of methyl hydrogen polysiloxane was dispersed, as ultraviolet shielding fine particles, in a mixture containing 22.7 wt. % of ethanol, 34.1 wt. % of methylcyclopolysiloxane ("SH245", product of Dow Corning Toray) and 3.0 wt. % of oxazoline-modified silicone (Preparation Example 1) in a homomixer ("Ultra Turrax T50/dispersing generator S50N-G45F/product of IKA in Japan), followed by dispersion treatment with a continuous-system sand mill ("Dyno Mill KDL-PILOT", product of WAB) filled with glass beads having a size of from 0.2 to 0.3 mm ("Unibeads 1113L", product of Union). The filling percentage of glass beads was 85% and peripheral speed of the sand mill upon agitation was 14 m/s. The mixture was supplied to the sand mill at a rate of 4.4 kg/h and dispersion treatment was performed five times. Cool water was circulated through a supply tank, receiver tank and jacket of the sand mill.

Example 1

Comparative Examples 1 to 3

Liquid ultraviolet protection cosmetic compositions (O/W emulsion cosmetic compositions) were prepared in accordance with the composition as shown in Table 1. The average particle size of Component (B) dispersed in water was measured and dispersion stability, ultraviolet protection effects and feeling upon use were evaluated. The results are shown collectively in Table 1.

(Preparation Process)

A uniform solution phase I was obtained by mixing and stirring Components (1) to (5). Then, Components (6) to (10) were mixed into Component (B) (prepared in a similar manner to Preparation Example 4), with which Component (11) was mixed and stirred, whereby a uniform solution phase II was obtained. The solution phase I was added to the solution phase II while stirring. To the reaction mixture were added other components (12), (13) and (14) successively. The resulting mixture was homogenized into a cosmetic composition.

(Evaluation Method)

(1) Measurement of Average Particle Size:

The average particle size of Component (B) dispersed in water was measured using a laser scattering particle size distribution analyzer. The average particle size of each cosmetic composition was measured after diluting it to an adequate concentration by purified water and then homogenizing the mixture by stirring.

(2) Dispersion Stability

Each cosmetic composition was filled in a 50-mL glass bottle and allowed to stand for 1 hour. The appearance of it was then observed by the naked eye and judged based on the following criteria:
A: The composition is dispersed well.
B: The composition is dispersed insufficiently.
C: The composition contains separated/precipitated powders.

(3) Ultraviolet Protection Effects:

The SPF value of each cosmetic composition was measured using an SPF analyzer (product of Optometrics) and evaluated in accordance with the following criteria.
A: SPF of 10 or greater.
B: SPF of 5 or greater but less than 10.
C: SPF less than 5.

(4) Feeling Upon Use

The feeling aroused by the application of an adequate amount of each cosmetic composition to the upper inner arm was evaluated in accordance with the following criteria.
A: refreshing and non-greasy feeling
B: less refreshing and non-greasy feeling
C: Neither refreshing nor non-greasy feeling

TABLE 1

| | Component (wt. %) | Ex. 1 | Comp. Ex. 1 | Comp. Ex. 2 | Comp. Ex. 3 |
|---|---|---|---|---|---|
| Phase I | 1 Oxazoline-modified silicone (Prep. Ex. 1) | 1.0 | 0 | 0 | 0 |
| | 2 Ethanol | 2.2 | 0 | 0 | 0 |
| | 3 Acrylic acid alkyl acrylate copolymer *1 | 0 | 0 | 1.0 | 0 |
| | 4 Alkyl-substituted polysaccharide derivative (Prep. Ex. 3) | 0 | 0 | 0 | 1.0 |
| | 5 Water | 0 | 0 | 30.0 | 30.0 |
| Phase II | 6 Silicone-covered fine zinc oxide particles *2 | 4.5 | 4.5 | 4.5 | 4.5 |
| | 7 Silicone-covered fine titanium oxide particles *3 | 0.8 | 0.8 | 0.8 | 0.8 |
| | 8 Oxazoline-modified silicone (Prep. Ex. 1) | 0.4 | 0.4 | 0.4 | 0.4 |
| | 9 Methylcyclopolysiloxane *4 | 4.5 | 4.5 | 4.5 | 4.5 |
| | 10 Ethanol | 3.0 | 3.0 | 3.0 | 3.0 |
| | 11 2-Ethylhexyl paramethoxycinnamate | 3.0 | 3.0 | 3.0 | 3.0 |
| | 12 Ethanol | 3.6 | 3.6 | 3.6 | 3.6 |
| | 13 Glycerin | 4.2 | 4.2 | 4.2 | 4.2 |
| | 14 Purified water | Balance | Balance | Balance | Balance |
| | Total | 100 | 100 | 100 | 100 |
| Evaluation | Average particle size (μm) | 0.533 | Unmeasurable | Unmeasurable | 15 |
| | Dispersion stability | A | C | C | A |
| | Ultraviolet protection effects | A | Unmeasurable | Unmeasurable | B |
| | Feeling upon use | A | Unmeasurabale | Unmeasurable | C |

*1: "PEMULEN TR-2" (product of Nikko Chemicals).
*2: obtained by covering fine zinc oxide particles ("ZnO-350", product of Sumitomo Osaka Cement) with 6 wt. % (corresponding to 1.3 mg/m$^2$) of methyl hydrogen polysiloxane.
*3: obtained by covering fine titanium oxide particles ("TTO-51A", product of Ishihara Sangyo Kaisha) with 8 wt. % (corresponding to 1.0 mg/m$^2$) of methyl hydrogen polysiloxane.
*4: "SH245" (product of Dow Corning Toray Silicone).

The cosmetic composition of Example 1, the invention product, had excellent dispersion stability and high ultraviolet protection effects and moreover, provided good feeling upon use. On the other hand, the cosmetic composition of Comparative Example 1 not containing the polymer (A) and the cosmetic composition of Comparative Example 2 using a polymer whose thickening effect had been lowered due to a metal oxide were not well dispersed and coagulation of powders occurred. The cosmetic composition of Comparative Example 3 using a polymer different from the polymer (A) had a large emulsion particle size and low ultraviolet protection effects. In addition, it did not provide a refreshing feeling because the dispersion stability of powders was brought by a thickening action.

Example 2

Sunscreen Lotion

A sunscreen lotion having the below-described composition was prepared in a similar manner to that employed in Example 1.

(Composition)

| | (wt. %) |
|---|---|
| Phase I | |
| (1) Oxazoline-modified silicone (Prep. Ex. 1) | 0.9 |
| (2) Ethanol | 2.1 |
| Phase II | |
| (3) Silicone-covered zinc oxide | 4.3 |
| (4) Silicone-covered titanium oxide | 0.7 |
| (5) Oxazoline-modified silicone (Prep. Ex. 1) | 0.35 |
| (6) Methylcyclopolysiloxane | 4.3 |
| (7) Ethanol | 2.9 |
| (8) 2-Ethylhexyl paramethoxycinnamate | 3.0 |

-continued

| | (wt. %) |
|---|---|
| Other components | |
| (9) Ethanol | 4.8 |
| (10) Glycerin | 5.0 |
| (11) Water | Balance |

The sunscreen lotion thus obtained had a viscosity of mPa·s ("B8L Viscometer", product of TOKI SANGYO CO., LTD., rotor No. 1, 30 rpm, 25° C.).

Example 3

Sunscreen Lotion

A sunscreen lotion having the below-described composition was prepared in a similar manner to that employed in Example 1.

(Composition)

|  | (wt. %) |
|---|---|
| Phase I | |
| (1) Oxazoline-modified silicone (Prep. Ex. 1) | 3.0 |
| (2) Ethanol | 7.0 |
| Phase II | |
| (3) Silicone-covered zinc oxide | 14.3 |
| (4) Silicone-covered titanium oxide | 2.4 |
| (5) Oxazoline-modified silicone (Prep. Ex. 1) | 1.2 |
| (6) Methylcyclopolysiloxane | 14.3 |
| (7) Ethanol | 9.6 |
| (8) 2-Ethylhexyl paramethoxycinnamate | 10.0 |
| Other components | |
| (9) Ethanol | 16.0 |
| (10) Glycerin | 16.7 |
| (11) Water | Balance |

The sunscreen lotion thus obtained had a viscosity of mPa·s ("B8L Viscometer", product of TOKI SANGYO CO., LTD., rotor No. 1, 30 rpm, 25° C.).

Example 4

Sunscreen Lotion

A sunscreen lotion having the below-described composition was prepared in a similar manner to that employed in Example 1.

(Composition)

|  | (wt. %) |
|---|---|
| Phase I | |
| (1) Oxazoline-modified silicone (Prep. Ex. 1) | 0.1 |
| (2) Ethanol | 0.2 |
| Phase II | |
| (3) Silicone-covered zinc oxide | 0.4 |
| (4) Silicone-covered titanium oxide | 0.1 |
| (5) Oxazoline-modified silicone (Prep. Ex. 1) | 0.04 |
| (6) Methylcyclopolysiloxane | 0.4 |
| (7) Ethanol | 0.3 |
| (8) 2-Ethylhexyl paramethoxycinnamate | 0.3 |
| Other components | |
| (9) Ethanol | 0.48 |
| (10) Glycerin | 0.5 |
| (11) Water | Balance |

The sunscreen lotion thus obtained had a viscosity of mPa·s ("B8L Viscometer", product of TOKI SANGYO CO., LTD., rotor No. 1, 30 rpm, 25° C.)

Example 5

Sunscreen Lotion

A sunscreen lotion having the below-described composition was prepared in a similar manner to that employed in Example 1.

(Composition)

|  | (wt. %) |
|---|---|
| Phase I | |
| (1) Polyoxyethylene•methylpolysiloxane copolymer ("Silicone SH3771", product of Down Corning Toray Silicone) | 1.0 |
| Phase II | |
| (2) Silicone-covered zinc oxide | 5.0 |
| (3) Polyoxyethylene•methylpolysiloxane copolymer ("Silicone SH3775", product of Down Corning Toray Silicone) | 1.0 |
| (4) Methylcyclopolysiloxane | 4.0 |
| (5) 2-Ethylhexyl paramethoxycinnamate | 3.0 |
| Other components | |
| (6) Ethanol | 3.0 |
| (7) Glycerin | 5.0 |
| (8) Water | Balance |

Example 6

Sunscreen Lotion

A sunscreen lotion having the below-described composition was prepared in a similar manner to that employed in Example 1.

(Composition)

|  | (wt. %) |
|---|---|
| Phase I | |
| (1) Oxazoline-modified silicone (Prep. Ex. 1) | 0.5 |
| (2) Polyoxyethylene (EO20) sorbitan monolaurate | 0.2 |
| (3) Ethanol | 1.2 |
| Phase II | |
| (4) Silicone-covered zinc oxide | 4.3 |
| (5) Silicone-covered titanium oxide | 0.7 |
| (6) Oxazoline-modified silicone (Prep. Ex. 1) | 0.35 |
| (7) Methylcyclopolysiloxane | 4.3 |
| (8) Ethanol | 2.9 |
| (9) 2-Ethylhexyl paramethoxycinnamate | 3.0 |
| Other components | |
| (10) Ethanol | 4.8 |
| (11) Glycerin | 5.0 |
| (12) Xanthan gum | 0.1 |
| (13) Water | Balance |

Example 7

Sunscreen Gel

A sunscreen gel having the below-described composition was prepared in a similar manner to that employed in Example 1.

(Composition)

|  | (wt. %) |
|---|---|
| Phase I | |
| (1) Oxazoline-modified silicone (Prep. Ex. 1) | 1.2 |
| (2) Ethanol | 2.8 |
| Phase II | |
| (3) Silicone-covered zinc oxide | 4.8 |
| (4) Silicone-covered titanium oxide | 0.8 |
| (5) Oxazoline-modified silicone (Prep. Ex. 2) | 0.7 |
| (6) Methylcyclopolysiloxane | 7.1 |
| (7) Ethanol | 6.6 |
| (8) 2-Ethylhexyl paramethoxycinnamate | 1.0 |
| Other components | |
| (9) Ethanol | 9.9 |
| (10) Glycerin | 5.0 |
| (11) Alkyl-substituted polysaccharide derivative (Prep. Ex. 3) | 0.5 |
| (12) Water | Balance |

Example 8

Non-Chemical Sunscreen Lotion

A non-chemical sunscreen lotion having the below-described composition was prepared in a similar manner to that employed in Example 1.

(Composition)

|  | (wt. %) |
|---|---|
| Phase I | |
| (1) Oxazoline-modified silicone (Prep. Ex. 1) | 0.9 |
| (2) Ethanol | 2.1 |
| Phase II | |
| (3) Silicone-covered zinc oxide | 4.3 |
| (4) Silicone-covered titanium oxide | 0.7 |
| (5) Oxazoline-modified silicone (Prep. Ex. 1) | 0.35 |
| (6) Methylcyclopolysiloxane | 4.3 |
| (7) Ethanol | 2.9 |
| (8) Squalane | 0.5 |
| (9) Neopentyl glycol dicaprate | 0.5 |
| Other components | |
| (9) Ethanol | 4.8 |
| (10) Glycerin | 5.0 |
| (11) Water | Balance |

As a result of evaluation of the dispersion stability, ultraviolet protection effects and feeling upon use as in Example 1, the cosmetic compositions obtained in Examples 2 to 8 were each excellent in dispersion stability, had high ultraviolet protection effects and provided a good feeling upon use.

The invention claimed is:

1. A cosmetic composition, comprising the following components (A), (B) and (C):
(A) a polymer which is a poly-N-acylethyleneimine-modified silicone composed of a hydrophobic monomer unit and a hydrophilic monomer unit and which contains from 40 to 80 wt. % of a hydrophilic group;
(B) a dispersion containing the following components (a), (b), (c) and (d):
(a) powders having ultraviolet screening ability and having a surface subjected to hydrophobic treatment,
(b) a polymer which is a poly-acylrthyleneimine-modified silicone composed of a hydrophobic monomer unit and a hydrophilic monomer unit and which contains from 40 to 80 wt. % of a hydrophilic group,
(c) a silicone oil, and
(d) an alcohol having from 1 to 3 carbon atoms, at an (a):(b):(c):(d) weight ratio of (from 25 to 65):(from 0.1 to 5):(from 10 to 50):(from 10 to 50); and
(C) water,
wherein said cosmetic composition comprises an O/W emulsion and said O/W emulsion comprises said components (A), (B), and (C).

2. The O/W emulsion cosmetic composition according to claim 1, further comprising from 0.01 to 10 wt. % of a (D) nonionic polymer composed of a hydrophilic monomer unit.

3. The O/W emulsion cosmetic composition according to claim 1 or 2, further comprising from 0.1 to 5 wt. % of a (E) nonionic surfactant.

4. An O/W emulsion cosmetic composition according to claim 1, wherein said polymer (A) has a molecular weight of 10000 to 250000.

5. An O/W emulsion cosmetic composition according to claim 1, m 1, wherein said polymer (A) has a molecular weight of 10000 to 200000.

6. An O/W emulsion cosmetic composition according to claim 1, wherein said polymer (A) is present in an amount of 0.1 to 10 wt. %, based on the weight of said composition.

7. An O/W emulsion cosmetic composition according to claim 1, wherein said polymer (A) is present in an amount of 0.2 to 5 wt. %, based on the weight of said composition.

8. An O/W emulsion cosmetic composition according to claim 1, wherein said powder (a) is at least one member selected from the group consisting of zinc oxide, titanium oxide, cerium oxide, and a mixture thereof.

9. An O/W emulsion cosmetic composition according to claim 1, wherein said powder (a) has an average particle size of 0.001 to 0.5 μm.

10. An O/W emulsion cosmetic composition according to claim 1, wherein said powder (a) has an average particle size of 0.01 to 0.1 μm.

11. An O/W emulsion cosmetic composition according to claim 1, wherein said silicone oil (c) is at least one member selected from the group consisting of dimethylpolysiloxane, methylcyclopolysiloxane, and a mixture thereof.

12. An O/W emulsion cosmetic composition according to claim 1, wherein said silicone oil (c) has a viscosity at 20° C. of from 1 to 1000 mm$^2$/s.

13. An O/W emulsion cosmetic composition according to claim 1, wherein said alcohol (d) is ethanol.

14. An O/W emulsion cosmetic composition according to claim 1, wherein said dispersion (B) comprises (a), (b), (c) and (d) at an (a):(b):(c):(d) weight ratio of (25 to 65):(0.5 to 4):(20 to 50):(10 to 50).

15. An O/W emulsion cosmetic composition according to claim 1, wherein said dispersion (B) is present in an amount of 1 to 50 wt.%, based on the weight of said composition.

16. An O/W emulsion cosmetic composition according to claim 1, wherein said dispersion (B) is present in an amount of 5 to 30 wt.% based on the weight of said composition.

17. An O/W emulsion cosmetic composition according to claim 1, wherein said polymer (A) and said polymer (b) are the same.

* * * * *

UNITED STATES PATENT AND TRADEMARK OFFICE
CERTIFICATE OF CORRECTION

PATENT NO. : 8,420,066 B2
APPLICATION NO. : 12/089611
DATED : April 16, 2013
INVENTOR(S) : Yukio Inomata et al.

It is certified that error appears in the above-identified patent and that said Letters Patent is hereby corrected as shown below:

In the Claims:

Column 14, line 5, "poly-acylrthyleneimine-modi-", should read --poly-N-acylethyleneimine-modi- --; and line 27, "claim 1, m 1, wherein", should read --claim 1, wherein--.

Signed and Sealed this
Twenty-fifth Day of June, 2013

Teresa Stanek Rea
*Acting Director of the United States Patent and Trademark Office*